United States Patent [19]

Saville

[11] Plant 5,090

[45] Aug. 23, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 382,622

[22] Filed: May 27, 1982

[51] Int. Cl.[3] ..... A01H 5/00

[52] U.S. Cl. ..... Plt./7

[58] Field of Search ..... Plt./7

*Primary Examiner*—James R. Feyrer

*Attorney, Agent, or Firm*—Vincent G. Gioia

[57] ABSTRACT

A new miniature rose variety of orange red and amber yellow coloring.

1 Drawing Figure

The present invention relates to a new and distinct variety of rose plant of the miniature rose class, which was originated by my crossing as seed parent the rose known as "Prominent" (U.S. Plant Pat. No. 3,380) and my seedling of (Sheri Anne×Glenfiddich) as pollen parent. The new rose is known by the denomination "Savor".

Among the novel characteristics possessed by this new variety which distinguish it from its parents and all other varieties of which I am aware are flowers of unusual orange red and yellow coloring. The flowers have amber yellow petal undersurface with orange red top surface coloring which predominates as blooms open and mature. Asexual reproduction by budding of the new variety as performed in Essex County, Mass., shows that the foregoing and other distinguishing characteristics come true to form and are established and transmitted through succeeding propagations.

The new and improved rose variety which I have developed features high centered, hybrid tea-like flowers borne singly and in small sprays of pleasing orange red and amber yellow coloring displayed on an erect, bushy and well-branched plant with abundant foliage.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "18B" is plate 18B of The Royal Horticultural Society Colour Chart.

Parentage: Seedling.

*Seed parent.*—"Prominent".

*Pollen parent.*—My unpatented, unreleased seedling of (Sheri Anne×Glenfiddich).

Class: Miniature.

The following observations are made of specimens grown under glass in Essex County, Mass. during the month of March.

FLOWER

Blooming habit: Recurrent.

A. Bud:

(1) *Size.*—Small.

(2) *Form.*—Long pointed.

(3) *Color.*—After sepals fall, amber yellow 18B petal undersurface (near to 19C) of main portion of the petal is first visible with yellow 14C at point of petal attachment. However, orange red colored petal edge of the petal top surface may also be seen. The orange red edge coloring varies from just at petal edge to washing into the petal undersurface in varying amounts with more washing seemingly on inner petals.

(4) *Sepals.*—Normal.

(5) *Penduncle.*—Length — $\frac{3}{4}$ to 1 inch. Aspect — straight. Strength — erect. Color — near 142B.

B. Bloom:

(1) *Size.*—Average size when fully expanded — about $1\frac{1}{2}$ inch.

(2) *Borne.*—Singly and small sprays.

(3) *Form.*—High centered, hybrid tea-like form.

(4) *Petalage.*—Number of petals under normal conditions — about 18.

(5) *Color.*—As flower opens, striking orange red-yellow bicoloring is seen with amber yellow petal undersurface remaining visible until about $\frac{1}{2}$ open stage and until inner petals unfurl. Predominant top petal surface coloring is orange red 34A, particularly at a distance. However, equally apparent on the petal top surface, especially on close inspection, are other orange red and brick red tones varying from orange red 34A to brick red 35C and 35D. More color washing is seen on petals at top and undersurface as they unfurl. The orange red coloring of the petal top surface extends to about $\frac{3}{4}$ of the petal. The coloring of the lower $\frac{1}{4}$ of the petal is yellow varying from Amber yellow 18A–18B at point of petal attachment to Naples yellow 11B until abruptly shading into the orange red coloring of the balance of the petal top surface.

C. Petals:

(1) *Texture.*—Thick.

(2) *Appearance.*—Inside and outside — satiny.

(3) *Form.*—Fan shaped.

(4) *Arrangement.*—Regularly arranged — shingle-like.

(5) *Petaloids in center.*—Few or none.

(6) *Persistence.*—Drop off cleanly.

(7) *Fragrance.*—Slight, sweet.

(8) *Lasting quality.*—Long lasting on plant and as cut flower.

REPRODUCTIVE ORGANS

A. Stamens, filaments and anthers:
(1) *Arrangement.*—Stamens regularly arranged around styles.
(2) *Color.*—Near 23A.

B. Pollen:
*Color.*—Near 23A to 24A.

C. Styles: Even, medium length.

D. Stigmas:
*Color.*—Near 157C.

E. Hips: None observed.

PLANT

A. Form: Erect, bushy, branched.

B. Growth: Vigorous, uniform branching attaining height of 16 to 18 inches.

C. Foliage: Compound 5 to 7 leaflets.
(1) *Size.*—Medium.
(2) *Quantity.*—Abundant.
(3) *Color.*—New foliage: Upper Side — near to 143A; Under side — near to 148B. Old foliage: Upper side — near to 137A; Under side — near 138C.
(4) *Shape.*—Oval, acute apices.
(5) *Texture.*—Upper side glossy and under side is matte.

(6) *Edge.*—Serrated.
(7) *Serration.*—Double serrate.
(8) *Leaf stem.*—Color — near to 145A. Under side — near 145B.
(9) *Stipules.*—Medium, smooth.
(10) *Resistance to disease.*—Blackspot — normal. Mildew — normal. Rust — normal.

D. Wood:
(1) *New wood.*—Color — near 146C. Bark — smooth.
(2) *Old wood.*—Color — near 146B. Bark — smooth.

E. Thorns:
(1) *Thorns.*—Quantity (main stalk) — ordinary. On laterals from stalk — normal. Form — long thin straight point. Length — small. Color — near 145C. Position — scattered.
(2) *Prickles.*—None.

F. Winter hardiness: Needs winter protection in severe climate.

I claim:

1. A new and distinct variety of rose plant of the miniature rose class, substantially as shown and described, characterized particularly by high-centered orange red and amber yellow flowers borne singly and in small sprays on a vigorous bushy plant.

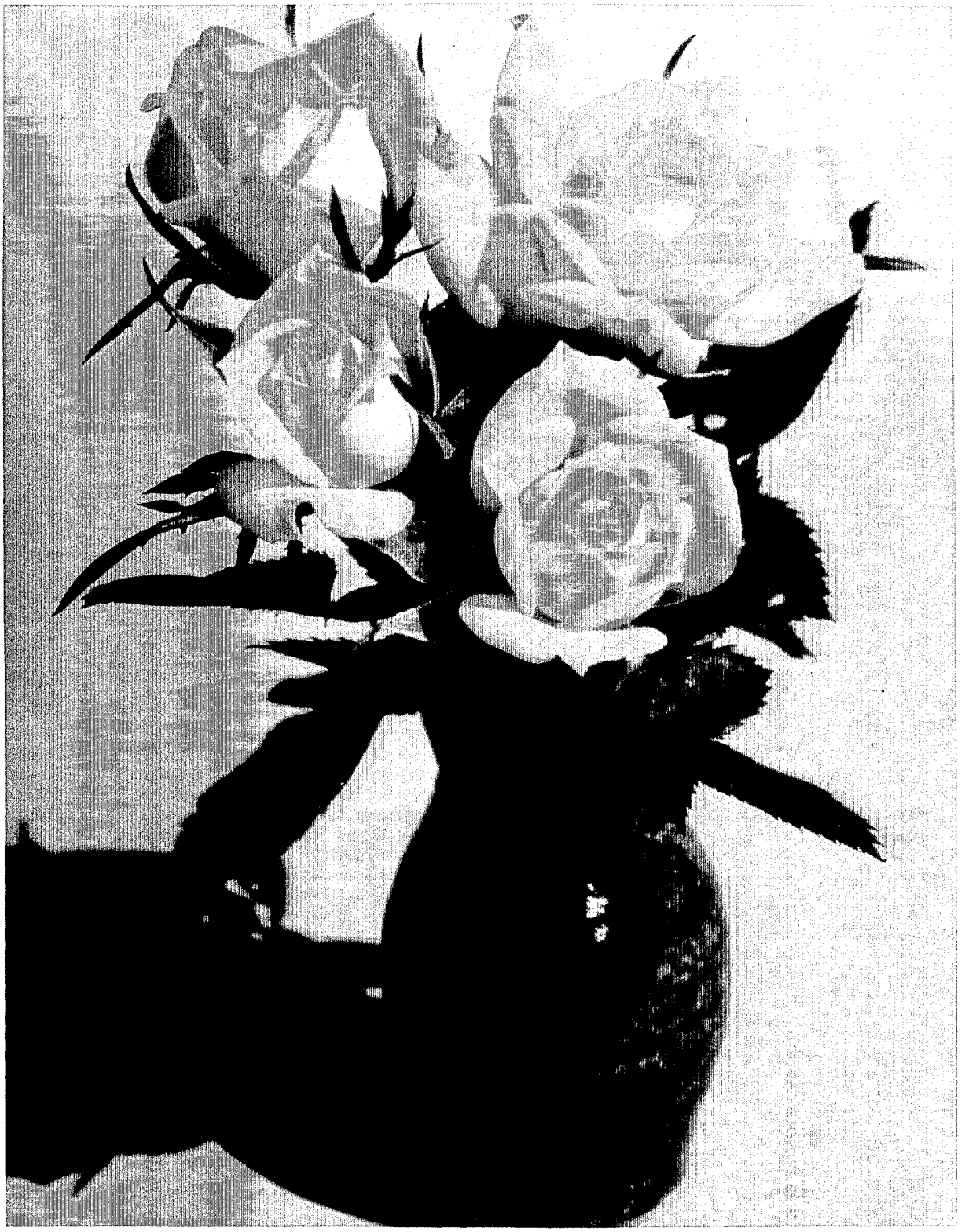

* * * * *